United States Patent [19]

Randin

[11] Patent Number: 4,557,690
[45] Date of Patent: Dec. 10, 1985

[54] ACCESSORY FOR USE IN DENTISTRY

[75] Inventor: Jean-Claude Randin, Ballaigues, Switzerland

[73] Assignee: Les Fils d'Auguste Maillefer Societe Anonyme A. Ballaigues, Vaud, Switzerland

[21] Appl. No.: 611,826

[22] Filed: May 18, 1984

[30] Foreign Application Priority Data

Jun. 3, 1983 [CH] Switzerland ............... 3064/83

[51] Int. Cl.³ ............................................. A61C 19/00
[52] U.S. Cl. ..................................... 433/49; 433/102; 221/288
[58] Field of Search ................... 433/49, 102, 53, 161; 221/263, 266, 288

[56] References Cited

U.S. PATENT DOCUMENTS 3,874,564  4/1975  Huneke ............................ 221/288
3,964,170  6/1976  Zdarsky ............................ 433/72

Primary Examiner—Robert Peshock
Attorney, Agent, or Firm—Silverman, Cass & Singer, Ltd.

[57] ABSTRACT

An accessory for use in pricking depth-indicating washers on to dental reamers comprises a body constituting a receptacle. The washers which are located in the receptacle are brought into a free space of the body within which they are juxtaposed. They successively engage a notch in a movable small plate, constituting a distributor element, which enables the washer located in the notch, by transverse sliding of the small plate, to be brought opposite to a hole of the body. The washer thus placed can easily be pricked by a dental canal reamer passing through a hole provided in the cover of the accessory and which is situated opposite to the hole of the body. The diameter of this hole is greater than that of the washers to allow the washer which is pricked on the spindle to be withdrawn from the receptacle.

7 Claims, 3 Drawing Figures

U.S. Patent   Dec. 10, 1985   4,557,690
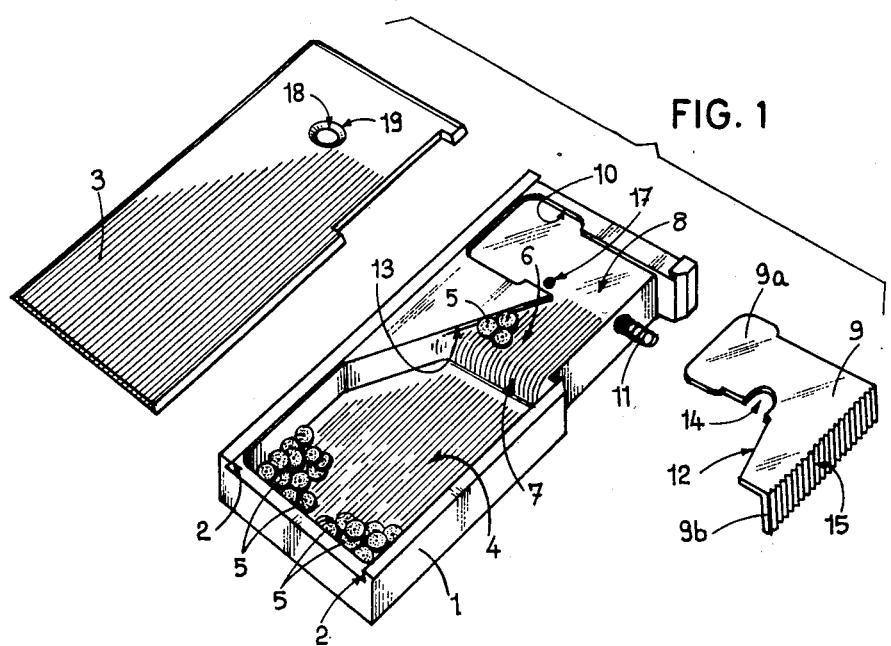
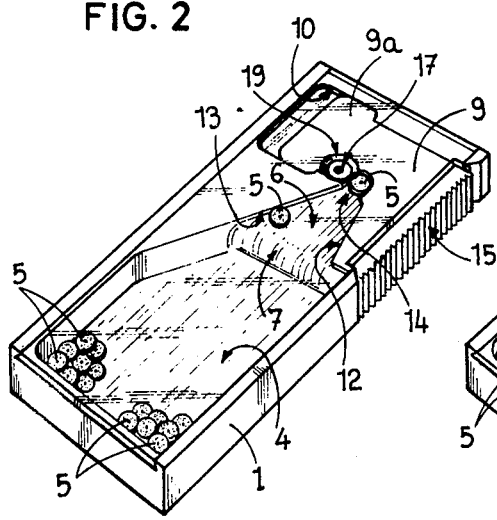
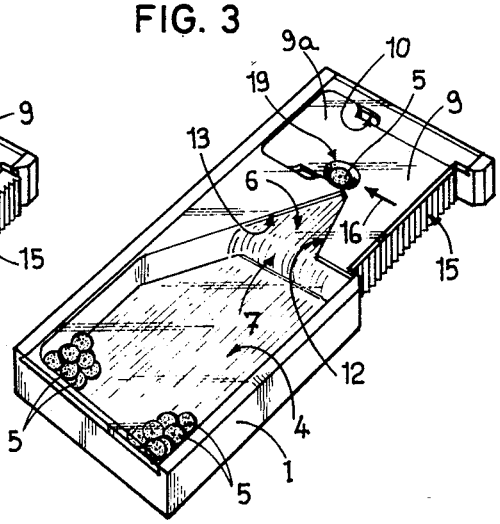

ACCESSORY FOR USE IN DENTISTRY

BACKGROUND OF THE INVENTION (a) Field of the Invention

This invention relates to an accessory for use in dentistry.

(b) Description of the Prior Art

The boring out of dental root canals is effected by means of reamers which must not be introduced into the root beyond a determined length. It is known to use, as a means of checking this length, small washers or pellets of silicone or of rubber which are pricked onto the canal reamers and which are positioned thereon to indicate the depth to which the boring must be effected.

It is often not easy for the dentist to grip these washers, the diameter of which is of some millimeters, and to hold them in a suitable position for pricking by a canal reamer.

SUMMARY OF THE INVENTION

The object of the invention is to provide a simple, efficient and cheap means enabling the operation of pricking a depth-indicating washer onto a canal reamer easily to be performed.

To this end, a dental accessory according to the invention comprises a body in which is provided a recess constituting a receptacle adapted to contain washers intended to be pricked on canal broaches so as to indicate the working depths of these spindles, said body being provided with distributing means arranged in such manner as to enable said washers to be brought successively into a position in which they are situated opposite an opening of the said body, whereby the washer thus positioned can be pricked by a canal reamer and can be withdrawn from the said receptacle, remaining pricked on said reamer.

The various features of the invention will be apparent from the following description, drawings and claims, the scope of the invention not being limited to the drawings themselves as the drawings are only for the purpose of illustrating a way in which the principles of the invention can be applied. Other embodiments of the invention utilising the same or equivalent principles may be used and structural changes may be made as desired by those skilled in the art without departing from the present invention and the purview of the appended claims.

BRIEF DESCRIPTION OF THE DRAWINGS

FIG. 1 is an exploded perspective view of an accessory in accordance with the invention, and FIGS. 2 and 3 are perspective views of this accessory illustrated in two different operating positions.

DESCRIPTION OF THE PREFERRED EMBODIMENTS

The accessory illustrated in the drawings comprises a parallelepipedic body 1, made of plastics material, the two long sides of which are provided with slide ways 2 for receiving a rectangular small plate 3 constituting a slide-on cover. This plate 3 is preferably transparent. A recess 4 is provided in the body 1 and constitutes a receptacle for washers or pellets 5, made of silicone or of rubber, intended to be pricked on dental canal reamers so as to serve as indicators of the working depth of the said reamers.

The body 1 is provided with a recess 6 constituting, with the cover 3, a free space communicating with the receptacle 4 and the height of which is slightly greater than the thickness of the washers 5. The connection between the receptacle 4 and the free space 6 is assured by a rounded transition portion 7 at the end of the bottom of the receptacle.

The free space 6 is prolongated by a recess 8 the height of which corresponds to that of the space 6, in which is located a small plate 9 provided with a head 9a situated in a widening 10 of this recess. The small plate 9 is held in place in the recess 8 by the cover 3 against which it bears. A coil spring 11, acting on an edge 9b of the small plate 9, urges the latter into its rest position, represented in FIG. 2, in which the head 9a bears on a shoulder at an end of the recess widening 10.

One of the edges, designated by reference 12, of the small plate 9 constitutes, with the lateral wall, designated by reference 13, of the free space 6, a dihedral the top of which is situated, when the small plate 9 occupies said rest position, opposite a notch 14 provided in the said small plate. When a pressure is exerted on the raised edge 9b of the small plate 9, which is knurled at 15, the small plate is displaced in the direction of the arrow 16 of FIG. 3 until the notch 14 is situated opposite a hole 17 in the body 1, the diameter of which is slightly more than that of the dental canal reamers.

A hole 18 provided in the cover 3 is situated, when the cover is in place on the body 1, opposite the hole 17 of the latter.

The accessory as described and illustrated is used as follows:

With the cover 3 removed or slid along to uncover the receptacle 4, the latter is supplied with washers 5. After the cover has been put back in place the body 1 is inclined so that washers 5, slipping along the rounded portion 7, enter into the space 6. The height of this space corresponding to the thickness of the washers, the latter cannot overlap one another in the space 6 but are juxtaposed therein. Due to the convergency of the opposed faces 12 and 13, one of the washers 5 engages the notch 14 of the small plate 9, as indicated in FIG. 2.

Then, the small plate 9 is displaced by pushing thereon with a finger of one hand so that this plate, operating as a distributor slide, brings the washer 5 located in the notch 14 opposite to the holes 17 and 18.

With the other hand, the dentist pricks this washer by means of a dental canal reamer, an operation which presents no difficulty since the washer is perfectly held and since, moreover, the hole 18 of the cover 3 is widened at 19, as shown in FIG. 1.

Then, the washer thus pricked on a dental canal reamer is extracted from the accessory, the hole 18 being of a diameter sufficient to allow the clear passage of the pricked washers.

I claim:

1. An accessory for use in dentistry comprising, a body including a recess for storing a plurality of washers to be positioned on a reamer for indicating the working depth of such reamer, a distributor mounted on said body, said recess having oppositely disposed walls which coverage at a location proximate said distributor, a passageway formed in said body at a location spaced from said recess, said distributor having a notch opening formed along an edge thereof, the distributor being slidably movable between a first position in which said notch is positioned opposite said converging walls and a second position in which said notch is positioned opposite said passageway in the body, whereby a selected washer is movable from said recess to a location between said converging walls into the notch opening of the distributor and thereafter into registry with said passageway in the body upon movement of the distributor from said first position to said second position thereof to permit the washer to be engaged by said reamer upon positioning the reamer within the passgeway.

2. An accessory as claimed in claim 1 in which said recess communicates with a free space provided in said body, the height of said free space corresponding substantially to the thickness of said washers so that, when the washers are moved from the recess into said free space, they do not overlap one another in the free space but are juxtaposed therein.

3. An accessory as claimed in claim 2 in which the bottom of the said recess is extended by a rounded portion leading into said free space so that upon tilting said body the washers are caused to enter the said free space.

4. An accessory as claimed in claim 2, in which said distributor comprises a plate the thickness of which corresponds to the height of said free space and which is movable in a depression provided in said body.

5. An accessory as claimed in claim 2, in which one edge of said plate forms one of said converging walls of said recess.

6. An accessory as claimed in claim 4 in which said plate is retained on said body by a cover which closes said recess, a hole formed in said cover in registry with said passageway, the diameter of the hole being greater than that of the washers.

7. An accessory as claimed in claim 1 including a return spring positioned between the body and a portion of the distributor to urge the distributor into its first position in which said notch is positioned opposite the top of the two converging walls of the recess.

* * * * *